US012692535B2

(12) United States Patent
Slatter

(10) Patent No.: US 12,692,535 B2
(45) Date of Patent: Jul. 28, 2026

(54) METHODS OF ENRICHING A TARGET SEQUENCE FROM A SEQUENCING LIBRARY USING HAIRPIN ADAPTORS

(71) Applicant: Illumina Cambridge Limited, Cambridge (GB)

(72) Inventor: Andrew Slatter, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 615 days.

(21) Appl. No.: 18/025,794

(22) PCT Filed: Sep. 10, 2021

(86) PCT No.: PCT/EP2021/074931
§ 371 (c)(1),
(2) Date: Mar. 10, 2023

(87) PCT Pub. No.: WO2022/053610
PCT Pub. Date: Mar. 17, 2022

(65) Prior Publication Data
US 2023/0416803 A1     Dec. 28, 2023

Related U.S. Application Data

(60) Provisional application No. 63/077,271, filed on Sep. 11, 2020.

(51) Int. Cl.
C12P 19/34 (2006.01)
C12N 15/10 (2006.01)
C12Q 1/6806 (2018.01)
(52) U.S. Cl.
CPC ....... *C12Q 1/6806* (2013.01); *C12N 15/1068* (2013.01)

(58) Field of Classification Search
CPC .................................................. C12Q 1/6869
See application file for complete search history.

(56) References Cited

U.S. PATENT DOCUMENTS

2017/0283864 A1* 10/2017 Ach ..................... C12Q 1/6855
2020/0010887 A1*  1/2020 Heron .................. C12Q 1/6869

FOREIGN PATENT DOCUMENTS

WO      2009/133466 A2   11/2009
WO      2015104302 A1     7/2015
(Continued)

*Primary Examiner* — Kenneth R Horlick
(74) *Attorney, Agent, or Firm* — Fletcher Yoder, P.C.

(57)      ABSTRACT
Disclosed herein is a method for enriching a sequencing library comprising double-stranded nucleic acid fragments comprising preparing a library of double-stranded fragments having one or more adaptors at ends of the double-stranded fragment; denaturing the double-stranded fragments to form single-stranded fragments; and hybridizing an extension primer that binds to a target sequence of at least one insert in the library of double-stranded fragments and that does not bind to non-target sequences. In an embodiment, the adaptor is a hairpin adaptor, and extension from the extension primer using a polymerase with 5' to 3' exonuclease activity removes all or part of a sequence of the hairpin adaptor that is at least partially complementary to the amplification primer sequence. Each fragment may comprise an insert comprising double-stranded nucleic acid and a hairpin adaptor at the 5' end of one or both strands of the double-stranded fragments. Hairpin adaptors may comprise an amplification primer sequence and a sequence at least partially complementary to the amplification primer sequence.

15 Claims, 7 Drawing Sheets

Specification includes a Sequence Listing.

(56)  References Cited

FOREIGN PATENT DOCUMENTS

| | | | |
|---|---|---|---|
| WO | 2015117040 | A1 | 8/2015 |
| WO | 2016025878 | A1 | 2/2016 |
| WO | 2017171985 | A1 | 10/2017 |
| WO | 2017203269 | A1 | 11/2017 |
| WO | 2017209891 | A1 | 12/2017 |
| WO | 2018015365 | A1 | 1/2018 |
| WO | 2018024671 | A1 | 2/2018 |
| WO | 2018045109 | A1 | 3/2018 |
| WO | 2018108328 | A1 | 6/2018 |
| WO | 2018175997 | A1 | 9/2018 |
| WO | 2020165180 | A1 | 8/2020 |

* cited by examiner

SEQUENCE LISTING

```
<160> NUMBER OF SEQ ID NOS: 2

<210> SEQ ID NO 1
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
tcgtcggcag cgtc                                                     14

<210> SEQ ID NO 2
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gtctcgtggg ctcgg                                                    15
```

METHODS OF ENRICHING A TARGET SEQUENCE FROM A SEQUENCING LIBRARY USING HAIRPIN ADAPTORS

CROSS-REFERENCE TO RELATED APPLICATIONS

This application is a national stage application claiming priority to PCT/EP2021/074931, which claims priority to and the benefit of U.S. Provisional Application No. 63/077, 271, entitled "METHODS OF ENRICHING A TARGET SEQUENCE FROM A SEQUENCING LIBRARY USING HAIRPIN ADAPTORS" and filed on Sep. 11, 2020, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Sep. 8, 2021, is named IP-2043-PCT_ SL.txt and is 806 bytes in size.

FIELD

This disclosure relates to preparation of enriching a target sequence from a sequencing library using hairpin adaptors.

BACKGROUND

Enriching a target sequence from a sequencing library can be hindered by slow and complex workflows. For example, library enrichment using hybridization capture methods requires amplification of a whole library before the hybridization capture step. In addition, conventional approaches of enrichment with targeted amplification can lose fragment end information.

The present methods use hairpin adaptors for enriching a target sequence from a sequencing library. In some cases, a single amplification step can enrich of a target sequence from a sequencing library. These methods with hairpin adaptors can avoid loss of fragment end information, which may be helpful for analysis of cell-free DNA and for fragment deduplication approaches.

SUMMARY

In accordance with the description, described herein are methods of enriching a target sequence from a sequencing library using a hairpin adaptor at the 5' end of one or both strands of double-stranded library fragments. Also described herein are forked adaptors and methods and kits for generating sequencing libraries with forked adaptors.

Disclosed herein is an adaptor for use in preparing a nucleic acid sequencing library comprising a first sequence having a 5' end and a 3' end; a second sequence having a 5' end and a 3' end; wherein a portion of the 3' end of the first sequence and a portion of the 5' end of the second sequence are complementary and form a first double-stranded region; wherein a portion of the 5' end of the first sequence and a portion of the 3' end of the second sequence are non-complementary; wherein the portion of the 5' end of the first strand includes a second double-stranded region.

In some embodiments, the second double-stranded region is a hairpin structure. In some embodiments, the second double-stranded region comprises a non-nucleic acid portion. In some embodiments, the non-nucleic acid portion is a linker. In some embodiments, the 5' end of the first strand includes a portion that is not degradable by an exonuclease. In some embodiments, the first double-stranded region is at least 5 consecutive nucleotides. In some embodiments, the second double-stranded region is at least 5 consecutive nucleotides. In some embodiments, the 5' end of the second strand is phosphorylated. In some embodiments, all cytosine bases in the first strand and in the second strand are methylated. In some embodiments, the adaptor further comprises a capture moiety.

Also described herein is a method of preparing a nucleic acid sequencing library comprising producing a plurality of double-stranded nucleic acid fragments; and attaching one or more forked adaptors to at least one end of the plurality of double-stranded nucleic acid fragments. In some embodiments, the adaptors are attached via tagmentation. In some embodiments, the adaptors are attached via ligation.

Also described herein is a kit for preparing a nucleic acid sequencing library comprising a forked adaptor; at least one primer capable of hybridizing to a portion of the adaptor; at least one enzyme; and dNTPs.

In some embodiments, the at least one enzyme has exonuclease activity. In some embodiments, the at least one enzyme is a polymerase. In some embodiments, at least one component is in a lyophilized or dried form.

Disclosed herein is a method for enriching a target sequence from a sequencing library of double-stranded fragments comprising preparing the sequencing library, wherein each fragment comprises an insert comprising double-stranded nucleic acid and a hairpin adaptor at the 5' end of one or both strands of the double-stranded fragments, wherein the hairpin adaptor comprises an amplification primer sequence and a sequence at least partially complementary to the amplification primer sequence; denaturing the double-stranded fragments to form single-stranded fragments; and, using a polymerase with 5'-3' exonuclease activity, producing a nucleic acid strand using an extension primer that binds to the target sequence comprised in at least one insert in the sequencing library; and removing all or part of the sequence at least partially complementary to the amplification primer sequence.

In some embodiments, the method further comprises amplifying fragments using an amplification primer that binds to the amplification primer sequence.

In some embodiments, the hairpin adaptor further comprises a linker between the amplification primer sequence and the sequence at least partially complementary to the amplification primer sequence. In some embodiments, said linker is not degradable by an exonuclease.

In some embodiments, the polymerase with 5'-3' exonuclease activity is Taq. In some embodiments, the extension primer and/or the polymerase used for producing a nucleic acid strand using an extension primer is removed after extension. In some embodiments, removing the extension primer and/or the polymerase used for producing a nucleic acid strand using an extension primer occurs by solid-phase reversible immobilization (SPRI) beads and/or by denaturing a heat-sensitive polymerase.

In some embodiments, producing a nucleic acid strand using an extension primer is performed with a reaction mixture comprising uracil. In some embodiments, the nucleic acid strand produced with a reaction mixture comprising uracil is cleaved by one or more uracil-specific excision reagent (USER). In some embodiments, USER is uracil DNA glycosylase and endonuclease VIII. In some embodiments, USER is a single enzyme with the activities of uracil DNA glycosylase and endonuclease VIII.

In some embodiments, a plurality of double-stranded fragments in the library do not comprise the target sequence. In some embodiments, said hairpin adaptor is comprised in double-stranded fragments of the library wherein all or part of the sequence at least partially complementary to the adaptor sequence is present. In some embodiments, a method further comprises, in a plurality of double-stranded fragments in the library that do not comprise the target sequence, cleaving the hairpin adaptor with a restriction endonuclease.

In some embodiments, the nucleic acid strand produced with a reaction mixture comprising uracil is resistant to restriction endonuclease digestion. In some embodiments, incorporation of uracil into a nucleic acid strand changes the sequence that was previously a restriction endonuclease cleavage site, thereby protecting the strand and its complement from cleavage. In some embodiments, the restriction endonuclease cleaves at a double-stranded nucleic acid formed by association of the amplification primer sequence with the sequence at least partially complementary to the amplification primer sequence.

Also described herein is a method for enriching a target sequence from a sequencing library of double-stranded fragments comprising preparing the sequencing library, wherein each fragment comprises an insert comprising double-stranded nucleic acid and a hairpin adaptor at the 5' end of one or both strands of the double-stranded fragments, wherein the hairpin adaptor comprises a first set of nucleotide sequences, wherein the first set of nucleotide sequences comprises an adaptor sequence and a sequence at least partially complementary to the adaptor sequence; a second set of nucleotide sequences, wherein the second set of nucleotide sequences comprises an amplification primer sequence and a sequence at least partially complementary to the amplification primer sequence, wherein the first set of nucleotide sequences is closer to the insert than the second set of nucleotide sequences; and a linker between the sequence at least partially complementary to the adaptor sequence and the sequence at least partially complementary to the amplification primer sequence; denaturing the double-stranded fragments to form single-stranded fragments; and, using a polymerase with 5'-3' exonuclease activity, (1) producing a nucleic acid strand using a first extension primer that binds to the target sequence comprised in at least one insert in the sequencing library, wherein the reaction mixture for producing the nucleic acid strand comprises uracil; and (2) removing all or part of the sequence at least partially complementary to the adaptor sequence; removing the first extension primer; providing USER; and, using a polymerase with 5'-3' exonuclease activity, (1) producing a nucleic acid strand using a second extension primer that binds to a target sequence comprised in at least one insert in the library of double-stranded fragments; and (2) removing all or part of the sequence at least partially complementary to the amplification primer sequence.

In some embodiments, a method further comprises amplifying fragments using an amplification primer that binds to the amplification primer sequence. In some embodiments, the complement of the amplification primer sequence and/or the linker between the sequence at least partially complementary to the adaptor sequence and the sequence at least partially complementary to the amplification primer sequence is not degradable by an exonuclease.

In some embodiments, the complement of the amplification primer sequence and/or the linker between the sequence at least partially complementary to the adaptor sequence and the sequence at least partially complementary to the amplification primer sequence comprises uracil.

In some embodiments, the method further comprises cleaving the hairpin adaptor with a restriction endonuclease after producing a nucleic acid strand using the first primer, wherein said hairpin adaptor is comprised in double-stranded fragments of the library wherein all or part of the sequence at least partially complementary to the adaptor sequence is present.

In some embodiments, the hairpin adaptor further comprises a linker between the amplification primer sequence and a sequence at least partially complementary to the amplification primer sequence.

In some embodiments, USER cleaves the nucleic acid strand generated by first primer extension, the linker comprised in the hairpin adaptor, and/or the sequence at least partially complementary to the adaptor sequence.

In some embodiments, the first and second extension primers bind to different sequences. In some embodiments, the first and second extension primers bind the same strand of the double-stranded nucleic acid.

In some embodiments, the polymerase with 5'-3' exonuclease activity is Taq. In some embodiments, the polymerase is removed before amplifying fragments.

In some embodiments, the second extension primer is removed after producing a nucleic acid strand using said primer. In some embodiments, the polymerase and/or second extension primer are removed using SPRI beads and/or by denaturing a heat-sensitive polymerase.

Also disclosed herein is a method for enriching a target sequence from a sequencing library of double-stranded fragments comprising preparing the sequencing library, wherein each fragment comprises an insert comprising double-stranded nucleic acid and a hairpin adaptor at the 5' end of one or both strands of the double-stranded fragments, wherein the hairpin adaptor comprises an amplification primer sequence and a sequence at least partially complementary to the amplification primer sequence; denaturing the double-stranded fragments to form single-stranded fragments; using a primer mix and an enzyme or enzymes with ligation activity and polymerase activity without 5'-3' exonuclease activity, (1) producing a nucleic acid strand using a first extension primer of a primer mix, wherein the primer mix comprises a first extension primer and a blocked second extension primer, wherein the first extension primer and the blocked second extension primer bind to different sequences of interest comprised in the double-stranded nucleic acid; and (2) ligating the nucleic acid strand produced using the first extension primer to the blocked second extension primer; removing primer mix not bound to an insert; deblocking the blocked second extension primer; and, using a polymerase with 5'-3' exonuclease activity, (1) producing a nucleic acid strand using the ligated first and second extension primers; and (2) removing all or part of the sequence at least partially complementary to the amplification primer sequence.

Also disclosed herein is a method for enriching a target sequence from a sequencing library of double-stranded fragments. The method includes preparing the sequencing library, wherein each fragment of the double-stranded fragments comprises an insert disposed between end adaptors, wherein each end adaptor comprises a first set of nucleotide sequences, wherein the first set of nucleotide sequences comprises an adaptor sequence and a sequence at least partially complementary to the adaptor sequence an amplification primer sequence extending away from a 3' terminus of the first set of nucleotide sequences. The method also includes denaturing the double-stranded fragments to form separated strands, each separated strand comprising a single-stranded portion of the insert; annealing sequence-specific extension primers to a complementary sequence in the single-stranded portion of the insert; extending a complementary strand from the annealed extension primers to form complementary strand and separated strand duplexes having double-stranded ends, the double-stranded ends comprising a 3' end of the complementary strand and a 5' end of the separated strand; ligating a double-stranded adaptor to each double-stranded end of the duplexes; denaturing the duplexes; and amplifying denatured strands of the duplexes to generate amplified products.

In some embodiments, the blocked second extension primer cannot produce a nucleic acid strand unless it is deblocked. In some embodiments, the blocked second extension primer binds a target sequence comprised in at least one insert and 5' of the sequence bound by the first extension primer. In some embodiments, the blocked second extension primer binds to the insert with a melting temperature of less than 60° C. In some embodiments, producing a nucleic acid strand using the ligated first and second extension primers is performed at a temperature of 60° C. or greater. In some embodiments, the annealing and extension temperature of the ligated first and second extension primers is above the melting temperature of the second extension primer. In some embodiments, the second extension primer is removed before amplifying. In some embodiments, the second extension primer is removed using SPRI beads or an exonuclease.

In some embodiments, one or more extension primer is a gene-specific primer.

In some embodiments, the hairpin adaptor is at the 5' end of one strand of double-stranded fragments. In some embodiments, the hairpin adaptor is at the 5' end of both strands of double-stranded fragments. In some embodiments, the hairpin adaptor is incorporated by ligation or tagmentation. In some embodiments, the amplification primer sequence and the sequence at least partially complementary to the amplification primer sequence each comprise at least 14 nucleotides. In some embodiments, the amplification primer sequence and the sequence at least partially complementary to the amplification primer sequence each comprise 14-60 nucleotides. In some embodiments, the hairpin adaptor comprises one or more enhancement to increase stability. In some embodiments, the hairpin adaptor comprises one or more modified or locked nucleic acids. In some embodiments, a modified nucleic acid comprises 8-aza-7-deazaguanosine. In some embodiments, the hairpin adaptor maintains association of the amplification primer sequence and the sequence at least partially complementary to the amplification primer sequence at temperatures of 60° C. or greater, 65° C. or greater, or 70° C. or greater.

In some embodiments, the amplification primer sequence comprises an A14, A14', B15, or B15' sequence. In some embodiments, the amplification primer cannot bind to the amplification primer sequence comprised in the hairpin adaptor when the amplification primer sequence is associated with the sequence at least partially complementary to the amplification primer sequence. In some embodiments, the sequence at least partially complementary to the amplification primer sequence comprises a sequence with 50% or greater, 60% or greater, 70% or greater, 80% or greater, 90% or greater, 95% or greater, or 99% or greater sequence identity with the complement of the amplification primer sequence. In some embodiments, the sequence at least partially complementary to the amplification primer sequence comprises the complement of the amplification primer sequence.

In some embodiments, one or both strands of double-stranded fragments comprise one or more additional adaptors 3' of the hairpin adaptor. In some embodiments, double-stranded fragments comprise one or more adaptors at the 3' end of one or both strands. In some embodiments, the one or more additional adaptors 3' of the hairpin adaptor and/or the one or more adaptors at the 3' end of one or both strands comprise a primer sequence, an index tag sequence, a capture sequence, a barcode sequence, a cleavage sequence, or a sequencing-related sequence, or a combination thereof.

In some embodiments, amplifying fragments using an amplification primer cannot destroy the hairpin adaptor. In some embodiments, the polymerase used for amplifying fragments using an amplification primer lacks 5'-3' exonuclease activity or wherein the polymerase used for amplifying fragments using an amplification primer is not a strand-displacing polymerase. In some embodiments, the polymerase used for amplifying fragments is Q5. In some embodiments, the amplification is bridge amplification.

In some embodiments, the method further comprises sequencing of amplified fragments. In some embodiments, the method allows sequencing of the full sequence of the insert.

In some embodiments, the double-stranded nucleic acid comprises DNA or RNA. In some embodiments, the double-stranded nucleic acid comprises cell-free DNA. In some embodiments, the method is used for fragment deduplication.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

DESCRIPTION OF THE SEQUENCES

Figure 1:
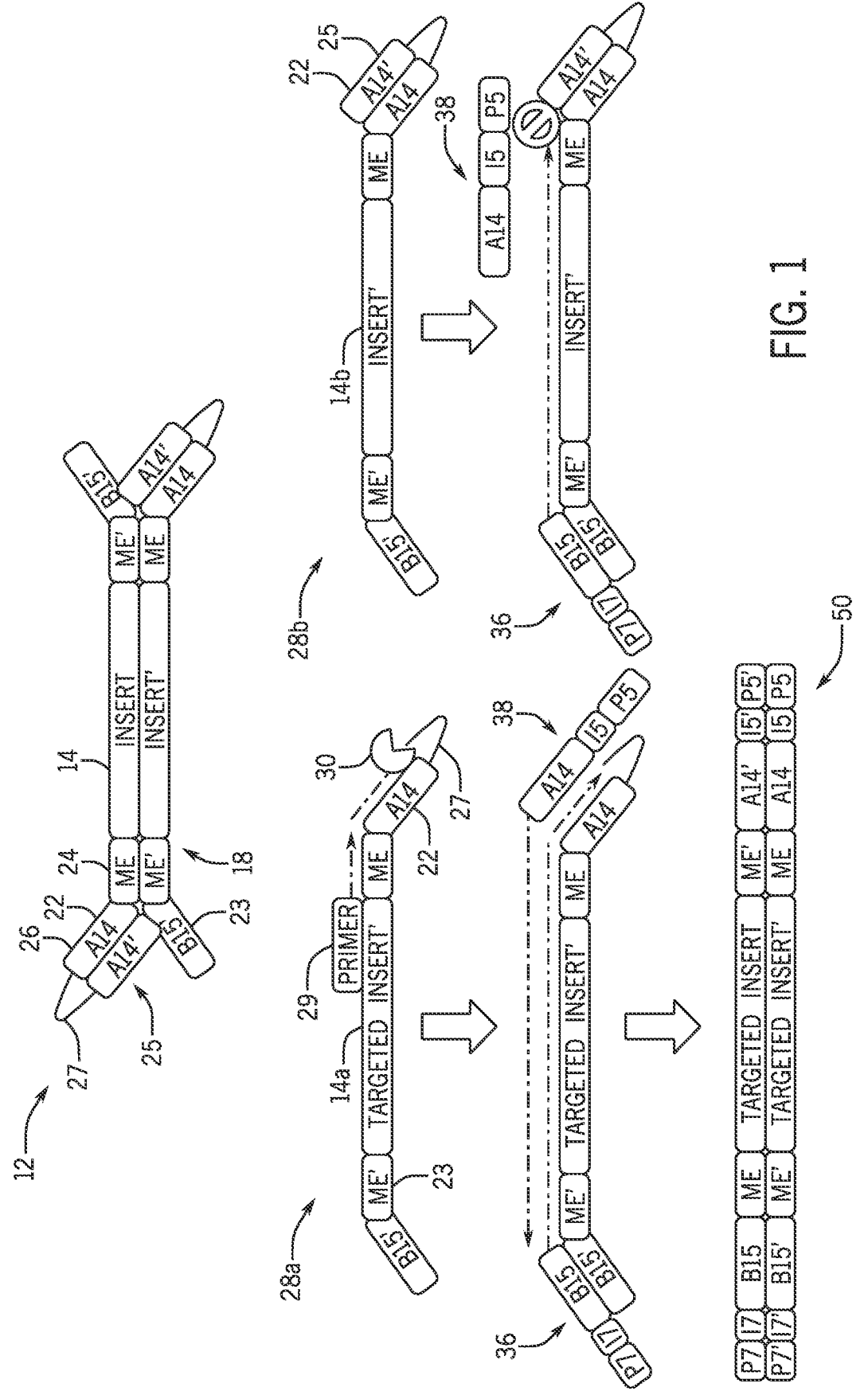
FIG. 1 shows a representative method of enriching a target sequence from a sequencing library using a hairpin adaptor at one or both 5' ends of a fragment contrasted with a non-target sequence.

Table 1 provides a listing of certain sequences referenced herein.

TABLE 1

Description of the Sequences

| Description | Sequences | SEQ ID NO |
|---|---|---|
| A14 | TCGTCGGCAGCGTC | 1 |
| B15 | GTCTCGTGGGCTCGG | 2 |

DESCRIPTION OF THE EMBODIMENTS

I. Adaptors for Use in Preparing a Nucleic Acid Sequencing Library and Library Preparation In some embodiments, adaptors are used to prepare a nucleic acid sequencing library.

In some embodiments, these adaptors are forked adaptors. As used herein, the term "forked adapter" means a double-stranded nucleic acid having a first end wherein the two strands are annealed to each other and a second end wherein the two strands are not annealed to each other. That is, forked adaptors include double-stranded and single-stranded regions. In an embodiment, an end of the forked adaptor is double-stranded. Examples of forked or Y-shaped adapters are described, for example, in U.S. Pat. Nos. 7,741,463, 10,253,359, and 9,868,982, each of which is incorporated herein by reference in its entirety.

In some embodiments, an adaptor for use in preparing a nucleic acid sequencing library comprises a first sequence having a 5' end and a 3' end; a second sequence having a 5' end and a 3' end; wherein a portion of the 3' end of the first sequence and a portion of the 5' end of the second sequence are complementary and form a first double-stranded region; wherein a portion of the 5' end of the first sequence and a portion of the 3' end of the second sequence are non-complementary; and wherein the portion of the 5' end of the first strand includes a second double-stranded region.

In some embodiments, the second double-stranded region is a hairpin structure. In some embodiments, the second double-stranded region comprises a non-nucleic acid portion. In some embodiments, the non-nucleic acid portion is a linker. In some embodiments, the 5' end of the first strand includes a portion that is not degradable by an exonuclease. In other words, the 5' end of the first strand may be exonuclease-resistant. In some embodiments, the first double-stranded region is at least 5 consecutive nucleotides. In some embodiments, the second double-stranded region is at least 5 consecutive nucleotides. In some embodiments, the 5' end of the second strand is phosphorylated. In some embodiments, all cytosine bases in the first strand and in the second strand are methylated. In some embodiments, the adaptor further comprises a capture moiety.

In some embodiments, a method of preparing a nucleic acid sequencing library comprises producing a plurality of double-stranded nucleic acid fragments; and attaching a forked adaptor to at least one end of the plurality of double-stranded nucleic acid fragments. In some embodiment, the one or more adaptors are attached via tagmentation. In some embodiments, the one or more adaptors are attached via ligation.

A wide variety of library preparations are known in the art, and the present method is not limited by the means of library generation. In some embodiments, the library is prepared using tagmentation or ligation. For example, tagmentation or ligation methods can be used to incorporate adaptors, e.g., hairpin adaptors, single-stranded adaptors, and/or double-stranded adaptors, at the ends of library fragments.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adaptor sequences at the ends of the fragments.

Preparation of a sequencing library via addition of forked adaptors via transposition is described in U.S. Pat. No. 10,246,746, which is incorporated herein by reference in its entirety.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

A "transposome complex," as used herein, is comprised of at least one transposase (or other enzyme as described herein) and a transposon recognition sequence. In some such systems, the transposase binds to a transposon recognition sequence to form a functional complex that is capable of catalyzing a transposition reaction. In some aspects, the transposon recognition sequence is a double-stranded transposon end sequence. The transposase binds to a transposase recognition site in a double-stranded nucleic acid and inserts the transposon recognition sequence into a double-stranded nucleic acid. In some such insertion events, one strand of the transposon recognition sequence (or end sequence) is transferred into the double-stranded nucleic acid, resulting in a cleavage event. Exemplary transposition procedures and systems that can be readily adapted for use with the transposases.

Tagmentation may be performed with immobilized or solution-phase transposome complexes.

Incorporation of adaptors by ligation is also well-known, as exemplified in workflows for Truseq sample preparation kits (Illumina, Inc.).

In some embodiments, a kit for preparing a nucleic acid sequencing library comprises a forked adaptor; at least one primer capable of hybridizing to a portion of the adaptor; at least one enzyme; and dNTPs. In some embodiments, the at least one enzyme has exonuclease activity. In some embodiments, the at least one enzyme is a polymerase. In some embodiments, at least one component of a kit is in a lyophilized or dried form.

II. Methods of Enriching a Target Sequence from a Sequencing Library Using Hairpin Adaptors Disclosed herein is a method for enriching a target sequence from a sequencing library using hairpin adaptors. As described below, an extension primer that binds to a target sequence and a polymerase with 5'-3' exonuclease activity can be used to specifically "unlock" hairpin adaptors and allow amplification of fragments comprising the target sequence (See FIG. 1).

In some embodiments, sequencing results are improved using the present methods because of the recovery of fragment ends during enriching, as compared to methods of enriching that may not recover fragment ends (such as direct targeted amplification using multiplex PCR).

In some embodiments, a method for enriching a target sequence from a sequencing library of double-stranded fragments comprises preparing the sequencing library, wherein each fragment comprises an insert comprising double-stranded nucleic acid and a hairpin adaptor at the 5' end of one or both strands of the double-stranded fragments, wherein the hairpin adaptor comprises an amplification primer sequence and a sequence at least partially complementary to the amplification primer sequence; denaturing the double-stranded fragments to form single-stranded fragments; and, using a polymerase with 5'-3' exonuclease activity, (1) producing a nucleic acid strand using an extension primer that binds to the target sequence comprised in at least one insert in the sequencing library; and (2) removing all or part of the sequence at least partially complementary to the amplification primer sequence.

In some embodiment, a hairpin adaptor comprises an amplification primer sequence and a sequence at least partially complementary to the amplification primer sequence.

The present methods have a variety of uses, such as for generating full sequences of fragmented nucleic acids, such as cell-free DNA. Further, the present methods can be used for fragment deduplication.

A. Target Sequences and Enriching a Target Sequence from a Sequencing Library

As used herein, a "target sequence" refers to any sequence of interest. For example, a target sequence may comprise a sequence comprised in a gene of interest, a specific mutation of interest, or any other sequence of interest to a user.

In some embodiments, in the absence of the present methods for enriching a target sequence from a sequencing library, a relatively low percentage of library fragments generated from a double-stranded nucleic acid may comprise the target sequence.

In some embodiments, a plurality of double-stranded fragments in the library do not comprise the target sequence before enriching. In some embodiments, a majority of double-stranded fragments in the library do not comprise the target sequence before enriching.

In some embodiments, enriching a target sequence from a sequencing library means that 2 or more-fold, 5 or more-fold, 10 or more-fold, 20 or more-fold, 50 or more-fold, 100 or more-fold, 1,000 or more-fold, 10,000 or more-fold, or 100,000 or more-fold more fragments comprising the target sequence are comprised in the library after enriching as compared to before enriching. The present methods may therefore be used to generate "enriched libraries." In some embodiments, the present methods allow high enrichment of small regions (i.e., few kilobase) of a double-stranded DNA comprised in a sample.

In some embodiments, the target sequence is comprised in a double-stranded nucleic used for library preparation. In some embodiments, the double-stranded nucleic may be comprised in any type of sample requiring target enrichment or wherein target enrichment would be beneficial. In some embodiments, the target sequence is comprised in cell-free DNA (cfDNA). In some embodiments, the target sequence is comprised in an oncology sample, such as a liquid biopsy sample. In some embodiments, the target sequence is comprised in an exome sample. In some embodiments, the target sequence is comprised in a rare and undiagnosed disease (RUGD) exome sample. In some embodiments, the target sequence is comprised in an RNA or cDNA library. In some embodiments, the target sequence is comprised in a methylation library.

B. Hairpin Adaptors Comprising Amplification Primer Sequences

As used herein, a "hairpin" refers to a nucleic acid comprising a pair of nucleic acid sequences that are at least partially complementary to each other. These two nucleic acid sequences that are at least partially complementary can bind to each other and mediate folding of a nucleic acid. In some embodiments, the two nucleic acid sequences that are at least partially complementary generate a nucleic acid with a hairpin secondary structure.

A "hairpin adaptor," as used herein, refers to an adaptor that comprises at least one pair of nucleic acid sequences that are at least partially complementary to each other. In some embodiments, a hairpin adaptor has a folded secondary structure.

FIG. 1 shows a library fragment comprising a double-stranded insert (insert and insert' sequences) with a hairpin adaptor at the 5' end of each strand. In the representative embodiment of FIG. 1, each hairpin adaptor comprises one pair of nucleic acid sequences that are at least partially complementary to each other (A14/A14'). In some embodiments, base pairing between a pair nucleic acid sequences that are at least partially complementary to each other "locks" the adaptor into a hairpin secondary structure. In such methods, the length of the extension primer used may be increased to improve specificity of the method to amplify fragments comprising the target sequence.

Figure 2:
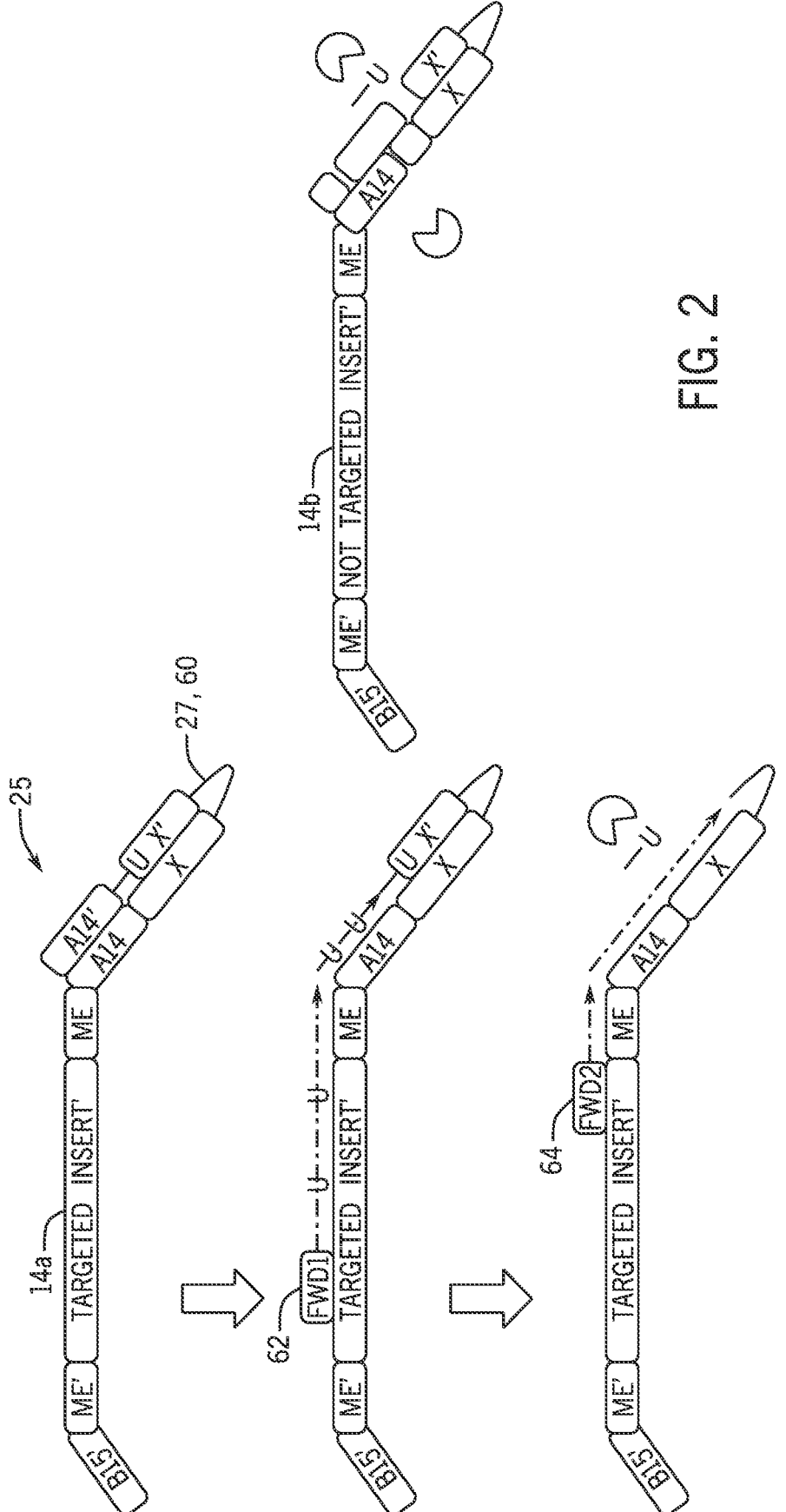
FIG. 2 shows how a hairpin adaptor can block amplification from an amplification primer sequence, in accordance with aspects of the present disclosure.

In some embodiments, a hairpin adaptor comprises more than one pair of nucleic acid sequences that are at least partially complementary to each other. In some embodiments, a hairpin adaptor comprises two pairs of nucleic acid sequences that are at least partially complementary to each other. In some embodiments, a hairpin adaptor comprises more than two pairs of nucleic acid sequences that are at least partially complementary to each other. FIG. 2 shows a hairpin adaptor comprising two pairs of nucleic acid sequences that are at least partially complementary to each other (the A14/14' pair and the X/X' pair).

In some embodiments, a hairpin adaptor comprises an amplification primer sequence. In some embodiments, a hairpin adaptor comprises an amplification primer sequence and all or part a sequence at least partially complementary to the adaptor sequence.

In some embodiments, a hairpin adaptor is "locked" (via base pairing between a pair nucleic acid sequences that are at least partially complementary to each other) unless all part of the sequence at least partially complementary to the amplification primer sequence is removed. In some embodiments, a locked hairpin prevents the polymerase from extending and generating the complement of the amplification primer sequence.

In some embodiments, the present methods block amplification of fragments not attached to a hairpin adaptor, because the hairpin adaptor comprises an amplification primer sequence that can be used for a later amplification step.

In this way, the present methods only allow amplification of library fragments that are attached to "unlocked" hairpin adaptors. Library fragments that were not attached to a hairpin adaptor and library fragments attached to "locked" hairpin adaptors would not be amplified. Such means of inhibiting amplification of undesired fragments (i.e., those not comprising a target sequence) can avoid costs and user time associated with downstream methods.

In some embodiments, the hairpin adaptor is at the 5' end of one strand of double-stranded fragments. In some embodiments, the hairpin adaptor is at the 5' end of both strands of double-stranded fragments. In some embodiments, the hairpin adaptor is incorporated by ligation or tagmentation. In some embodiments, the amplification primer sequence and the sequence at least partially complementary to the amplification primer sequence each comprise at least 14 nucleotides. In some embodiments, the amplification primer sequence and the sequence at least partially complementary to the amplification primer sequence each comprise 14-60 nucleotides. In some embodiments, the hairpin adaptor comprises one or more enhancement to increase stability. In some embodiments, the hairpin adaptor comprises one or more modified or locked nucleic acids. In some embodiments, a modified nucleic acid comprises 8-aza-7-deazaguanosine. In some embodiments, the hairpin adaptor maintains association of the amplification primer sequence and the sequence at least partially complementary to the amplification primer sequence at temperatures of 60° C. or greater, 65° C. or greater, or 70° C. or greater.

In some embodiments, the amplification primer sequence comprises an A14 sequence (SEQ ID NO: 1) or B15 sequence (SEQ ID NO: 2), or their complements (A14' or B15', respectively).

In some embodiments, the sequence at least partially complementary to the amplification primer sequence comprises a sequence with 50% or greater, 60% or greater, 70% or greater, 80% or greater, 90% or greater, 95% or greater, or 99% or greater sequence identity with the complement of the amplification primer sequence. In some embodiments, the sequence at least partially complementary to the amplification primer sequence comprises the complement of the amplification primer sequence.

1. Adaptors

Figure 5:
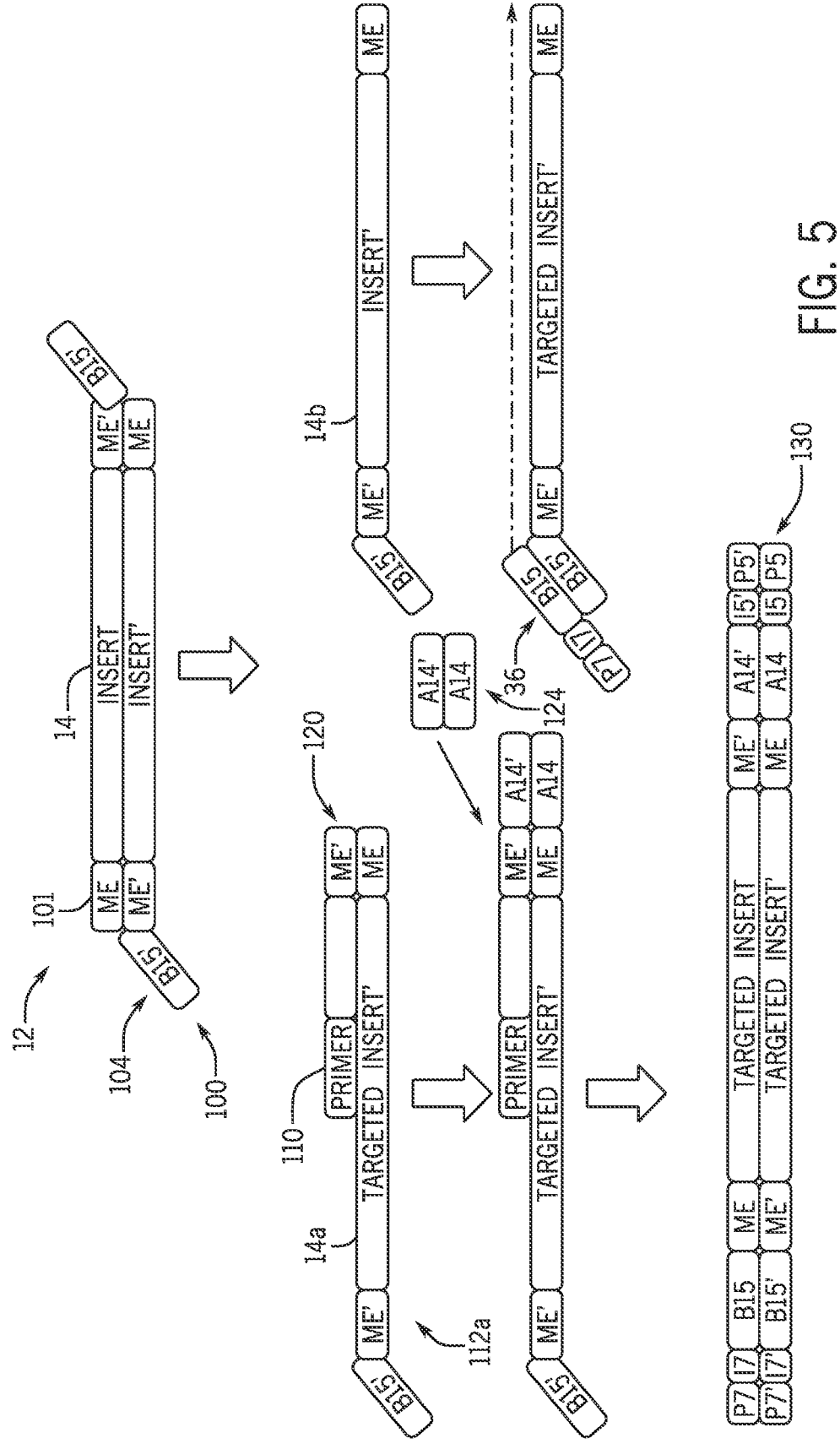
FIG. 5 shows a representative method of enriching a target sequence from a sequencing library using a double-stranded adaptor ligated to an end of a target insert-containing fragment contrasted with no adaptor ligation, and thus no bidirectional amplification, from fragments that do not contain target inserts, in accordance with aspects of the present disclosure.

In some embodiments, library fragments comprise one or more adaptors in addition to or in alternative to the hairpin adaptors, such as a symmetrical single adaptor that is provided only on both 5' ends or only on both 3' ends of a double-stranded library fragment (FIG. 5). In an embodiment, the symmetrical single adaptor creates a single-stranded end of a double-stranded library fragment. In an embodiment, the symmetrical single adaptor is a B15 or B15' adaptor. In an embodiment, the symmetrical single adaptor is a A14 or A14' adaptor.

In some embodiments, one or both strands of double-stranded fragments comprise one or more additional adaptors 3' of the hairpin adaptor. In some embodiments, double-stranded fragments comprise one or more adaptors at the 3' end of one or both strands.

In some embodiments, the adaptor sequence comprises a primer sequence, an index tag sequence, a capture sequence, a barcode sequence, a cleavage sequence, or a sequencing-related sequence, or a combination thereof. As used herein, a sequencing-related sequence may be any sequence related to a later sequencing step. A sequencing-related sequence may work to simplify downstream sequencing steps. For example, a sequencing-related sequence may be a sequence that would otherwise be incorporated via a step of ligating an adaptor to nucleic acid fragments. In some embodiments, the adaptor sequence comprises a P5 or P7 sequence (or their complement) to facilitate binding to a flow cell in certain sequencing methods.

In some embodiments, the amplification primer sequence comprised in the hairpin is a universal primer sequence. A universal sequence is a region of nucleotide sequence that is common to, i.e., shared by, two or more nucleic acid molecules.

In some embodiments, the hairpin adaptor further comprises a linker between the amplification primer sequence and the sequence at least partially complementary to the amplification primer sequence. In some embodiments, this linker is a nucleotide linker. In some embodiments, this linker is a non-nucleotide linker. In some embodiments, this linker is a synthetic linker. In some embodiments, this linker is not degradable by an exonuclease (i.e., the linker is exonuclease-resistant) such that exonuclease activity terminates at the linker.

C. Double-Stranded Nucleic Acids

In some embodiments, double-stranded nucleic acids used to generate libraries are composed of DNA, RNA, or analogs thereof. In some embodiments, the source of the acids is genomic DNA, messenger RNA, or other nucleic acids from native sources. In some embodiments, the nucleic acids that are derived from such sources can be amplified prior to use in a method described herein.

Exemplary biological samples from which double-stranded nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlanyydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dicoostelium discoideum*; a fungi such as *Pneumocystis carinii, Takifugu rubripes*, yeast, *Saccharamoyces cerevisiae* or *Schkosaccharomyces pombe*; or a Plasmodium falciparum. Double-stranded nucleic acids can also be derived from a prokaryote such as a bacterium, such as *Escherichia coli, staphylococci*, or *Mycoplasma pneumoniae*; an archae; a virus such as Hepatitis C virus or human immunodeficiency virus; or a viroid. Double-stranded nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al, Molecular Cloning: A Laboratory Manual, 3rd edition, Cold Spring Harbor Laboratory, New York (2001) or in Ausubel et al, Current Protocols in Molecular Biology, John Wiley and Sons, Baltimore, Md. (1998), each of which is incorporated herein by reference.

In some embodiments, double-stranded nucleic acids can be obtained as fragments of one or more larger nucleic acids.

Fragmentation can be carried out using any of a variety of techniques known in the art including, for example, nebulization, sonication, chemical cleavage, enzymatic cleavage, or physical shearing.

A population of double-stranded nucleic acids, or amplicons thereof, can have an average strand length that is desired or appropriate for a particular application of the methods or compositions set forth herein. For example, the average strand length can be less than 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for population of double-stranded nucleic acids, or amplicons thereof, can be in a range between a maximum and minimum value set forth above. It will be understood that amplicons generated at an amplification site (or otherwise made or used herein) can have an average strand length that is in a range between an upper and lower limit selected from those exemplified above.

In some embodiments, the double-stranded nucleic acids have a relatively short average strand length, such as less than 200 nucleotides, less than 150 nucleotides, less than 100 nucleotides, less than 75 nucleotides, less than 50 nucleotides, or less than 36 nucleotides. Examples of sample types with relatively short average strand length are cell-free DNA (cfDNA) and exome sequencing sample.

In some embodiments, the double-stranded nucleic acids are cell-free DNA (cfDNA) from a maternal blood sample. In some embodiments, the cfDNA is extracted from a maternal plasma sample. In some embodiments, the cfDNA is for noninvasive prenatal testing (NIPT). In some embodiments, the double-stranded nucleic acids are exomes. In some embodiments, the exomes are from a sample from a patient with a suspected rare and undiagnosed disease (RUGD).

D. Extension Primers

As used herein, "extension" when used in reference to a primer is intended to include processes wherein one or more nucleotides are added to the primer (e.g. via polymerase activity) or wherein one or more oligonucleotides are added to the primer (e.g. via ligase activity).

In some embodiments, one or more extension primer binds to a target sequence comprised in at least one insert in the library of double-stranded fragments. Using a polymerase with 5'-3' exonuclease activity, a method may comprise (1) producing a nucleic acid strand using the extension primer; and (2) removing all or part of the sequence at least partially complementary to the amplification primer sequence in the hairpin adaptor (as shown in FIG. 1). In some embodiments, a locked hairpin prevents the polymerase from extending and generating the complement of the amplification primer sequence in the nucleic acid strand produced. Thus, binding of the extension primer to an insert comprising the target sequence allows selective "unlocking" of the hairpin adaptor on this fragment.

In some embodiments, one or more extension primer is a gene-specific primer. For example, an extension primer may bind to a target sequence in a cancer gene to allow enriching for this target sequence from the sequencing library.

In some embodiments, methods use a single extension primer. In some embodiments, methods use more than one extension primer.

In some embodiments, an extension primer has a melting temperature of 60° C. or greater. In some embodiments, an extension primer has a melting temperature of 60° C. or greater, 65° C. or greater, or 70° C. or greater. In some embodiments, an extension primer with a melting temperature of 60° C. or greater allows a "hot start" reaction to decrease non-specific binding. In some embodiments, the melting temperature of an extension primer is controlled by the length of the primer, the GC content, or other factors well-known to those in the art.

In some embodiments, more than one extension primer are used in a single step of, using a polymerase with 5'-3' exonuclease activity, producing a nucleic acid strand using an extension primer that binds to a target sequence comprised in at least one insert in the library of double-stranded fragments and removing all or part of the sequence at least partially complementary to the amplification primer sequence. In some embodiments, multiple extension primers are used in a single step of the method. For example, multiple extension primers may bind to different target sequences within a gene of interest or to different genes of interest.

Figure 4:
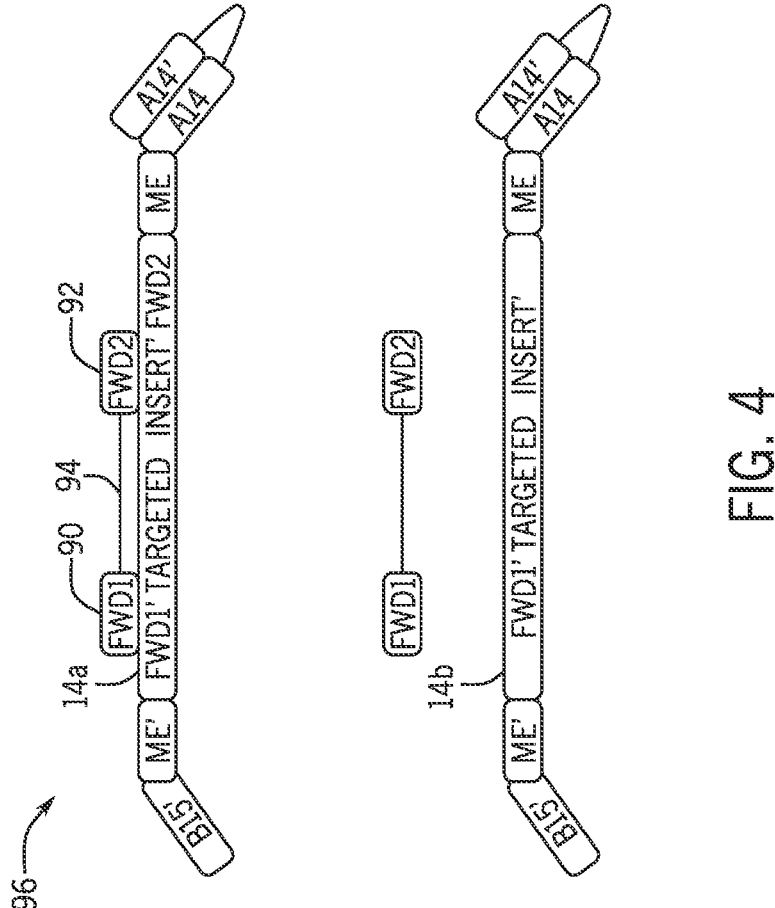
FIG. 4 shows a method wherein the first and second extension primer (each binding different target sequences) are linked via a linker, in accordance with aspects of the present disclosure.

In some embodiments, multiple extension primers are linked via one or more linker (i.e., such as shown in FIG. 4). In some embodiments, two extension primers are linked via a linker. In some embodiments, multiple extension primers linked via one or more linker have a higher melting temperature. In some embodiments, multiple extension primers linked via one or more linker one bind to inserts that comprise target sequences capable of binding each extension primer (for example, fwd1' and fwd2' as shown in FIG. 4).

In some embodiments, two extension primers may be ligated together during the method, as described below.

In some embodiments, different extension primers are used in different steps of the method.

E. Polymerase with 5'-3' Exonuclease Activity

In some embodiments, the method comprises, using a polymerase with 5'-3' exonuclease activity, producing a nucleic acid strand using an extension primer that binds to a target sequence comprised in at least one insert in the library of double-stranded fragments and removing all or part of the sequence at least partially complementary to the amplification primer sequence.

In some embodiments, the 5'-3' exonuclease activity of the polymerase mediates removing all or part of the sequence at least partially complementary to the amplification primer sequence. In some embodiments, the polymerase with 5'-3' exonuclease activity cleaves all or part of the sequence at least partially complementary to the amplification primer sequence. In some embodiments, a locked hairpin prevents the polymerase from extending and generating the complement of the amplification primer sequence in the nucleic acid strand produced.

In some embodiments, the polymerase with 5'-3' exonuclease activity is Taq. In some embodiments, the extension primer and/or the polymerase used for producing a nucleic acid strand using an extension primer is removed after extension. In some embodiments, removing the extension primer and/or the polymerase used for producing a nucleic acid strand using an extension primer occurs by solid-phase reversible immobilization (SPRI) beads. In some embodiments, the polymerase is a heat-sensitive polymerase that be removed by denaturing. In some embodiments, the heat-sensitive polymerase is full-length Bst or DNA polymerase I.

F. Amplification

In some embodiments, the method further comprises amplifying fragments using an amplification primer that binds to the amplification primer sequence. In some embodiments, only fragments wherein all or part of the sequence at least partially complementary to the amplification primer sequence has been removed can be amplified. In some embodiments, a locked hairpin prevents the polymerase from extending and generating the complement of the amplification primer sequence.

In some embodiments, amplification primers may comprise index sequences (See, for example, i5 and i7 index sequences in FIG. 1). These index sequences may be used to identify the sample and location in the array. In some embodiments, an index sequence comprises a unique molecular identifier (UMI). UMIs are described in Patent Application Nos. WO 2016/176091, WO 2018/197950, WO 2018/197945, WO 2018/200380, and WO 2018/204423, each of which is incorporated herein by reference in its entirety.

In some embodiments, amplifying fragments using an amplification primer cannot destroy the hairpin adaptor. In some embodiments, the polymerase used for amplifying fragments using an amplification primer lacks 5'-3' exonuclease activity or the polymerase used for amplifying fragments using an amplification primer is not a strand-displacing polymerase. In some embodiments, the polymerase used for amplifying fragments is Q5. In some embodiments, the amplification is bridge amplification.

In some embodiments, samples are amplified on a solid support.

For example, in some embodiments, samples are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, in some embodiments via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example, one or more clusters or colonies can be formed via solid-phase PCR whether one or both primers of each pair of amplification primers are immobilized.

In other embodiments, samples are amplified in solution. For example, in some embodiments, samples are cleaved or otherwise liberated from a solid support and amplification primers are then hybridized in solution to the liberated molecules. In other embodiments, amplification primers are hybridized to desired samples for one or more initial amplification steps, followed by subsequent amplification steps in solution. In some embodiments, an immobilized nucleic acid template can be used to produce solution-phase amplicons.

It will be appreciated that any of the amplification methodologies described herein or generally known in the art can be utilized with universal or target-specific primers to amplify desired samples. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify immobilized DNA fragments. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference) technologies. It will be appreciated that these amplification methodologies can be designed to amplify immobilized DNA fragments. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest. As a non-limiting example of primer extension and ligation primers that can be specifically designed to amplify a nucleic acid of interest, the amplification can include primers used for the Golden-Gate assay (Illumina, Inc., San Diego, CA) as exemplified by U.S. Pat. Nos. 7,582,420 and 7,611,869, each of which is incorporated herein by reference in its entirety.

Exemplary isothermal amplification methods that can be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'->3' exo- for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety.

G. Sequencing

In some embodiments, the method further comprises sequencing of amplified fragments. In some embodiments, the method allows sequencing of the full sequence of the insert. The ability to generate the full sequence of inserts is in contrast to methods with direct targeted amplification (such as multiplex PCR), as portions of inserts beyond where the primer binds can be lost with direct targeted amplification.

Sequencing after enriching methods described herein can be performed using a variety of different methods.

One exemplary sequencing methodology is sequencing-by-synthesis (SBS). In SBS, extension of a nucleic acid primer along a nucleic acid template is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Flow cells provide a convenient solid support for sequencing. For example, to initiate a first SBS cycle, one or more labeled nucleotides, DNA polymerase, etc., can be flowed into/through a flow cell that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons.

Thus, the sequencing reaction can be monitored via a luminescence detection system. Excitation radiation sources used for fluorescence-based detection systems are not necessary for pyrosequencing procedures. Useful fluidic systems, detectors and procedures that can be adapted for application of pyrosequencing to amplicons produced according to the present disclosure are described, for example, in WIPO Pat. App. Pub. No. WO 2012058096, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and $\gamma$-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the nucleic acid or individual nucleotides removed from a nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. Nos. 7,582, 420; 6,890,741; 6,913,884 or 6,355,431 or US Pat. Pub. Nos. 2005/0053980 A1; 2009/0186349 A1 or US 2005/0181440 A1, each of which is incorporated herein by reference.

An advantage of the methods set forth herein is that they provide for rapid and efficient detection of a plurality of nucleic acid in parallel. Accordingly, the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines, and the like. A flow cell can be configured and/or used in an integrated system for detection of nucleic acids. Exemplary flow cells are described, for example, in US 2010/0111768 A1 and US Pub. No. 2012/0270305 A1, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in US Pub. No. 2012/0270305, which is incorporated herein by reference.

III. Enriching a Target Sequence from a Sequencing Library Using Hairpin Adaptors and Uracil Specific Excision Reagents or Restriction Endonucleases Hairpin adaptors described herein can be used in a number of different workflows. For example, various different workflows can be used to increase the presence of fragments comprising the target sequence and/or reduce the presence of fragments not comprising the target sequence.

A. Nucleic Acid Strands Comprising Uracil and Uracil Specific Excision Reagents

Some restriction enzymes cannot cleave nucleic acid strands comprising uracil. In some embodiments, replacing a thymine within a restriction endonuclease cleavage site inhibits cleavage by the endonuclease. (See Glenn et al. Biotechniques 17(6): 1086-1090.) In some embodiments, methods comprise generating a nucleic acid strand that comprises uracil and that is resistant to restriction enzyme digestion, as shown in FIG. 2.

In some embodiments, a uracil in the nucleic acid strand comprising uracil replaces a thymine in a restriction endonuclease cleavage site.

In some embodiments, a nucleic acid strand comprising uracil comprises all or part of the sequence at least partially complementary to the amplification primer sequence, thereby making a double-stranded nucleic acid comprising the amplification primer sequence and the sequence at least partially complementary to it resistant to restriction endonuclease cleavage.

In some embodiments, a polymerase with 5'-3' exonuclease activity can incorporate uracil.

In some embodiments, a method comprises use of one or more uracil specific excision reagents (USER). A USER can cleave a nucleic acid strand comprising uracil.

In some embodiments, producing a nucleic acid strand using an extension primer is performed with a reaction mixture comprising uracil. In some embodiments, the nucleic acid strand produced with a reaction mixture comprising uracil is cleaved by one or more USER. In some embodiments, USER is uracil DNA glycosylase and endonuclease VIII. In some embodiments, USER is a single enzyme with the activities of uracil DNA glycosylase and endonuclease VIII.

In some embodiments, the nucleic acid strand produced with a reaction mixture comprising uracil is resistant to restriction endonuclease digestion.

B. Restriction Endonucleases

In some embodiments, a method further comprises, in a plurality of double-stranded fragments in the library that do not comprise the target sequence, cleaving the hairpin adaptor with a restriction endonuclease.

In some embodiments, the restriction endonuclease cleaves at a double-stranded nucleic acid formed by association of the amplification primer sequence with the sequence at least partially complementary to the amplification primer sequence.

In some embodiments, the restriction endonuclease cleaves at a double-stranded nucleic acid formed by association of an adaptor sequence with the sequence at least partially complementary to the adaptor sequence (See, for example, cleavage of A14/A14' in FIG. 2).

In some embodiments, the efficiency of cleavage by a restriction endonuclease decreases with increasing amount of uracil comprised a double-stranded DNA sequence comprising the endonuclease's cleavage site. In some embodiments, the restriction endonuclease cannot cleave one or more double-stranded nucleic acid comprising uracil.

In some embodiments, the cleavage site of the restriction endonuclease comprises a thymine. In some embodiments, incorporation of uracil in a nucleic acid strand changes the sequence that was previously a restriction endonuclease cleavage site, thereby protecting the strand and its complement from cleavage. In some embodiments, the restriction enzyme cleaves the hairpin adaptor and generates an overhang. In some embodiments, the restriction enzyme cleaves the hairpin adaptor and generates a blunt end.

C. Methods Comprising USER and Hairpin Adaptors Comprising More Than One Set of Sequences that are at Least Partially Complementary In some embodiments, a method for enriching a target sequence from a sequencing library of double-stranded fragments comprises preparing the sequencing library, wherein each fragment comprises an insert comprising double-stranded nucleic acid and a hairpin adaptor at the 5' end of one or both strands of the double-stranded fragments, wherein the hairpin adaptor comprises a first set of nucleotide sequences, wherein the first set of nucleotide sequences comprises an adaptor sequence and a sequence at least partially complementary to the adaptor sequence; a second set of nucleotide sequences, wherein the second set of nucleotide sequences comprises an amplification primer sequence and a sequence at least partially complementary to the amplification primer sequence, wherein the first set of nucleotide sequences is closer to the insert than the second set of nucleotide sequences; and a linker between the sequence at least partially complementary to the adaptor sequence and the sequence at least partially complementary to the amplification primer sequence; denaturing the double-stranded fragments to form single-stranded fragments; using a polymerase with 5'-3' exonuclease activity, producing a nucleic acid strand using a first extension primer that binds to the target sequence comprised in at least one insert in the sequencing library, wherein the reaction mixture for producing the nucleic acid strand comprises uracil; and removing all or part of the sequence at least partially complementary to the adaptor sequence; removing the first extension primer; providing USER; and, using a polymerase with 5'-3' exonuclease activity, (1) producing a nucleic acid strand using a second extension primer that binds to a target sequence comprised in at least one insert in the library of double-stranded fragments; and (2) removing all or part of the sequence at least partially complementary to the amplification primer sequence. A representative example of such a method is shown in FIG. 2.

In some embodiments, the complement of the amplification primer sequence and/or the linker between the sequence at least partially complementary to the adaptor sequence and the sequence at least partially complementary to the amplification primer sequence is exonuclease-resistant.

In some embodiments, the complement of the amplification primer sequence and/or the linker between the sequence at least partially complementary to the adaptor sequence and the sequence at least partially complementary to the amplification primer sequence comprises uracil.

In some embodiments, the method further comprises cleaving the hairpin adaptor with a restriction endonuclease after producing a nucleic acid strand using the first primer, wherein said hairpin adaptor is comprised in double-stranded fragments of the library wherein all or part of the sequence at least partially complementary to the adaptor sequence is present and does not comprise uracil.

In some embodiments, the nucleic acid strand produced using the first primer extension comprises uracil and is resistant to restriction endonuclease digestion.

In some embodiments, the hairpin adaptor further comprises a linker between the amplification primer sequence and a sequence at least partially complementary to the amplification primer sequence. In some embodiments, this linker is not degradable by an exonuclease. In some embodiments, this linker is synthetic. In some embodiments, this linker comprises a uracil or otherwise acts to pause polymerase activity.

In some embodiments, USER cleaves the nucleic acid strand generated by first primer extension, the linker comprised in the hairpin adaptor, and/or the sequence at least partially complementary to the adaptor sequence. In some embodiments, the nucleic acid strand generated by first primer extension, the linker comprised in the hairpin adaptor, and/or the sequence at least partially complementary to the adaptor sequence comprise one or more uracil.

In some embodiments, the first and second extension primers bind to different sequences. In some embodiments, the first and second extension primers bind the same strand of the double-stranded nucleic acid.

In some embodiments, the second extension primer is removed after producing a nucleic acid strand using said primer. In some embodiments, the polymerase and/or second extension primer are removed using SPRI beads. In some embodiments, the polymerase is a heat-sensitive polymerase that be removed by denaturing. In some embodiments, the heat-sensitive polymerase is full-length Bst or DNA polymerase I.

IV. Enriching a Target Sequence from a Sequencing Library Using Hairpin Adaptors and Ligation of Multiple Extension Primers In some embodiments, a method for enriching a target sequence from a sequencing library comprises preparing the sequencing library, wherein each fragment comprises an insert comprising double-stranded nucleic acid and a hairpin adaptor at the 5' end of one or both strands of the double-stranded fragments, wherein the hairpin adaptor comprises an amplification primer sequence and a sequence at least partially complementary to the amplification primer sequence; denaturing the double-stranded fragments to form single-stranded fragments; using a primer mix and an enzyme or enzymes with ligation activity and polymerase activity without 5'-3' exonuclease activity, producing a nucleic acid strand using a first extension primer of a primer mix, wherein the primer mix comprises a first extension primer and a blocked second extension primer, wherein the first extension primer and the blocked second extension primer bind to different sequences of interest comprised in the double-stranded nucleic acid; and ligating the nucleic acid strand produced using the first extension primer to the blocked second extension primer; removing primer mix not bound to an insert; deblocking the blocked second extension primer; and, using a polymerase with 5'-3' exonuclease activity, (1) producing a nucleic acid strand using the ligated first and second extension primers; and (2) removing all or part of the sequence at least partially complementary to the amplification primer sequence.

In some embodiments, the blocked second extension primer cannot produce a nucleic acid strand unless it is deblocked. In some embodiments, the blocked second extension primer comprises a block such that extension cannot occur unless the block is removed. In some embodiments, the block is the presence of a 3' phosphate on the blocked second primer. In some embodiments, the blocked second primer is deblocked by a kinase that cleaves the 3' phosphate. In some embodiments, the deblocked second extension primer can produce a nucleic acid strand.

In some embodiments, the blocked second extension primer binds a target sequence comprised in at least one insert and 5' of the sequence bound by the first extension primer.

In some embodiments, the second extension primer binds to the insert with a melting temperature of less than 60° C. In other words, the second extension primer may have relatively weak binding to the insert. In other words, the second extension primer may have relatively weak binding to the insert, whether or not the second extension primer is blocked or not. In some embodiments, the second extension primer dissociates from the insert at temperatures above 60° C., above 65° C., or above 70° C.

In some embodiments, the second extension primer and a polymerase produce less nucleic acid strand when a "hot start" extension protocol is used, as compared to a standard extension protocol. In some embodiments, the second extension primer and a polymerase produce less nucleic acid strand when the temperatures is above 60° C., above 65° C., or above 70° C. In some embodiments, the second extension primer and a polymerase cannot produce a nucleic acid strand at temperatures above 60° C., above 65° C., or above 70° C.

In some embodiments, the ligated first and second extension primers bind to the insert with a melting temperature of 60° C. or greater. In other words, the ligated first and second extension primers may have relatively strong binding to the insert. In some embodiments, the ligated first and second extension primers remain associated with the insert at temperatures above 60° C., above 65° C., or above 70° C. In some embodiments, producing a nucleic acid strand using the ligated first and second extension primers is performed at a temperature of 60° C. or greater. In some embodiments, producing a nucleic acid strand using the ligated first and second extension primers is performed at a temperature of 60° C. or greater, 65° C. or greater, or 70° C. or greater. In some embodiments, the annealing and extension temperature of the ligated first and second extension primers is above the melting temperature of the second extension primer.

In some embodiments, the second extension primer is removed before amplifying. In some embodiments, the second extension primer is removed using SPRI beads or an exonuclease.

EXAMPLES

Example 1. Enriching a Target Sequence from a Sequencing Library Using Hairpin Adaptors Methods with hairpin adaptors can be used for enriching a target sequence from a sequencing library. FIG. 1 shows an example double-stranded fragment 12 that is a representative fragment of a sequencing library formed from a plurality of fragments 12 with respective different inserts 14. Each fragment 12 includes an adaptor 18 at both ends. In the illustrated embodiment, the adaptors 18 are the same. The adaptors are forked adaptors, with a first strand 22 and a second strand 23. The first strand 22 and that second strand 23 form a double-stranded region 24. The first strand also includes a hairpin region 25 having a hairpin double-stranded region 26 and a linker 27 that is disposed between the self-complementary portions of the double-stranded region 26.

In the specific example of FIG. 1, the hairpin region 25 includes A14 and its complement A14'. Base pairing of A14/A14' within the double-stranded region 26 means that the A14 primer sequence is not available for binding to an amplification primer when the hairpin region 25 is intact. In this example, the double-stranded region 26 of the hairpin region 25 comprises an A14 primer sequence and its complement (A14').

The workflow shown in FIG. 1 includes a step of denaturing the fragments 12 to yield positive and negative strands. In the illustrated example, the negative strand 28 is shown. However, it should be understood that the workflow steps also apply to the positive strand in embodiments. If the fragment 12 contains a targeted insert 14a of interest, a strand 28a binds to an extension primer 29 that is complementary to a portion of the targeted insert 14a. The A14' sequence of the hairpin region 25 is removed using a polymerase 30 with 5'-3' exonuclease activity (such as Taq). The polymerase 30 causes the formerly double-stranded region 26 to be single-stranded, making the A14 sequence available.

The polymerase 30 is then removed. Full extension from a first amplification primer 36 is possible to copy the strand 28a, and a second amplification primer 38 is bound to the A14' in the generated nucleic acid strand to specifically amplify fragments comprising inserts comprising the target sequence. In this method, there is no amplification of fragments without hairpin adaptors (through failed fragment generation) or fragments or strands, such as strand 28b, wherein the hairpin adaptor and hairpin region 25 is "locked" (i.e., the A14 and A14' sequences of the hairpin are associated with each other). The locked hairpin prevents the polymerase from extending over A14; therefore, fragments that comprise the hairpin cannot generate a nucleic acid strand comprising A14' and cannot therefore be amplified by the A14 primer. The length of the extension primer in this method may be increased to ensure specificity for binding to inserts comprising the insert' sequence. The i5 and i7 sequences represent index sequences, which may be used to identify the sample and location in the array. ME=mosaic end sequence (the sequence in a transposon needed for the transposase to integrate the transposon into a target sequence) and ME'=complement of the mosaic end sequence. Amplification yields full length products 50 that include targeted inserts 14 with different sequencing primers and indexes at respective ends.

To enrich a target sequence from a sequencing library, the user can generate extension primers (i.e., target probes) that bind to one or more target sequences in a double-stranded DNA. Using known means of library generation and tagging (such as Nextera, Truseq, etc.) the hairpin-containing adaptor 18 can be added to one or both 5' end of the double-stranded fragments.

The double-stranded fragments of the library can be denatured. Then, using a polymerase with 5'-3' exonuclease activity, (1) a nucleic acid strand can be produced using an extension primer that binds to the target sequence comprised in at least one insert in the library of double-stranded fragments and (2) all or part of the A14' sequence can be removed.

In fragments wherein the A14' sequence of the hairpin has been removed (i.e., the hairpin has been unlocked), an amplification primer can be then used to selectively amplify fragments with unlocked hairpin adaptors. Using this method, only fragments with unlocked hairpins will be amplified. Fragments comprising hairpins wherein all or part of the A14' sequence of the hairpin is intact would not be amplified. In the unamplified example that includes the non-target insert 14b shown in FIG. 1, the A14 sequence in the hairpin adaptor is base paired with a complementary A14' sequence. When the hairpin adaptor is intact, an amplification primer cannot bind to the amplification primer sequence, because of the "locked" hairpin secondary structure. Thus, the non-target insert is not amplified.

In the method shown in FIG. 1, when a first strand is amplified (using a primer comprising B15') a nucleic acid strand comprising A14' is generated (shown as the dashed line). After denaturing the newly generated strand from the library fragment, an amplification primer comprising A14 is then able to bind to A14' for amplification (shown as A14 binding to the dashed strand of FIG. 1).

Example 2. Enriching a Target Sequence from a Sequencing Library Using Hairpin Adaptors and User Reagents Enriching a target sequence from a sequencing library can be performed using a "double unlock" method (FIG. 2). In this representative method, the hairpin region 25 includes a linker 27 that is a synthetic linker 60, such as one comprising uracil, or a uracil in the X' sequence. Sequential use of two extension primers (fwd1 62 and fwd2 64) that bind target sequences in the targeted inserts 14a allows increased enrichment of a target sequence from a sequencing library by using "double unlock" (sequential removal of A14' and then removal of X'). In this sequential method, the first nucleic acid strand comprises uracil. A restriction endonuclease can be used to cleave the A14/A14' sequence in hairpin adaptors wherein the A14' sequence has not been removed and replaced with a sequence comprising uracil. The restriction endonuclease step can be used to remove inserts that do not comprise the target sequence (i.e., the fragments comprising "not targeted insert'").

Using this this method, greater enriching a target sequence from a sequencing library may be seen, based on steps in the method to increase specificity. This method uses two extension primers (fwd1 and fwd2), which can both bind to target sequences that may be comprised in a single insert. In other words, fwd1 and fwd2 may bind to target sequences that are spatially close in a double-stranded DNA sample.

The hairpin adaptor in this method comprises 2 sets of complementary nucleic acids (A14/A14' and X/X' in FIG. 2). In this embodiment, A14 is an adaptor (and A14' is its complement) and X is an amplification primer sequence (and X' is its complement). Further, X' and/or the linker between X' and A14' comprise a uracil or are otherwise exonuclease-resistant.

Library fragments are denatured and an extension primer is added (fwd1). Then, using a polymerase with 5'-3' exonuclease activity (such as Taq), (1) a nucleic acid strand is produced using fwd1, wherein the reaction mixture for producing the nucleic acid strand comprises uracil NTPs, and (2) all or part of A14' is removed. Thus, the nucleic acid strand produced comprises uracil and is resistant to restriction endonuclease cleavage.

The fwd1 primers are removed (by exonuclease or SPRI beads).

In addition, a restriction enzyme can cleave any hairpin adaptors wherein A14' was not removed and replaced with a nucleic acid strand comprising uracil. As shown in FIG. 2, a nucleic acid strand comprising uracil can block the A14 sequence from cleavage by the restriction endonuclease. In contrast, those hairpin adaptors on library fragments wherein no nucleic acid strand was produced comprising uracil (i.e., those fragments comprising an insert that did not bind the fwd1 primer) are cleaved by the restriction endonuclease.

USER can then be used to cleave the nucleic acid strand comprising uracil and/or the uracil in the synthetic linker (between A14' and X') or in X'. A fwd2 primer can then bind and, using a polymerase with 5'-3' exonuclease activity (such as Taq), (1) a nucleic acid strand is produced using fwd2 that binds to a target sequence, and (2) all or part of X' is removed. Now that X' is removed, an amplification primer can be used that binds to X can selectively amplify fragments comprising inserts that can bind both fwd1 and fwd2. This method has increased specificity, as it comprises separate unlocking steps mediated by fwd1 and fwd2 primers (to remove A14' and then X') and also comprises a restriction endonuclease cleavage of intact hairpin adaptors comprising A14/A14' without uracil.

Figure 3:
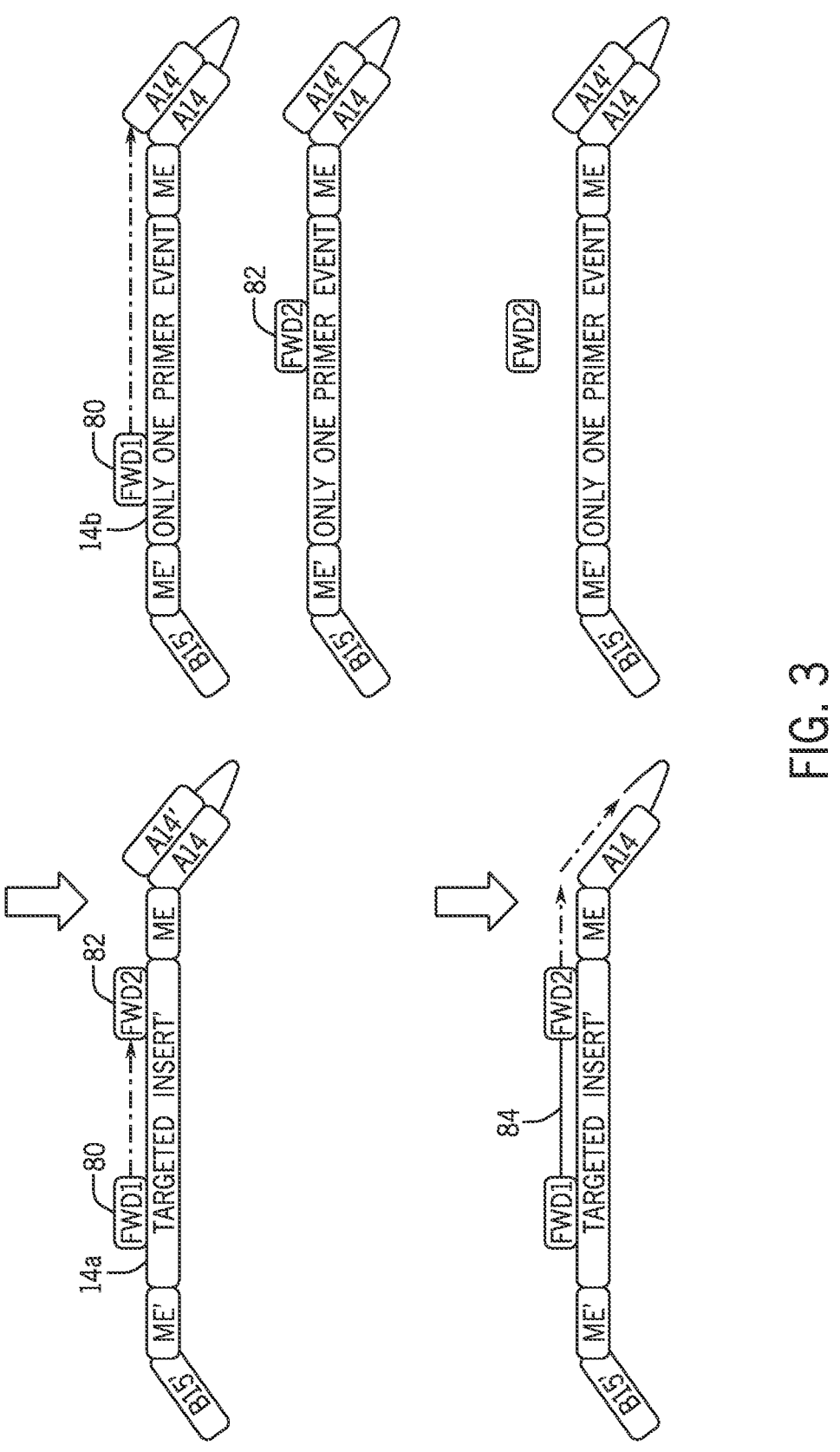
FIG. 3 shows a method wherein the hairpin adaptor comprises 2 sets of nucleotide sequences that that are at least partially complementary (A14/A14' and X/X'), in accordance with aspects of the present disclosure.

Example 3. Enriching a Target Sequence from a Sequencing Library Using Hairpin Adaptors and Ligation of Two Extension Primers In this method, two extension primers 80, 82 are used (fwd1 and fwd2) that both bind target sequences within inserts of interest. That is, as shown in FIG. 3, the fwd1 and fwd2 extension primers respectively bind to different, e.g., noncontiguous regions of an individual targeted insert sequence 14a. Using a polymerase without exonuclease activity and a ligase, a ligated fwd1 and fwd2 structure 84 is generated. This ligated primer can be used for a hot start extension reaction after fwd2 is deblocked. That is, the fwd2 primer is blocked, such that it cannot mediate extension. In this case, initial extension is performed with an enzyme mix comprising a ligase and a polymerase without exonuclease activity. Such a mix of a polymerase without exonuclease activity and a ligase may be an ELM mix (such as that provided in Illumina DNA PCR-Free Library Prep kit #1000000086922). Thus, extension from fwd1 ligates a nucleic acid strand between fwd1 and fwd2, without cleaving fwd2.

The ligated fwd1-fwd2 primer will bind with high affinity to the insert, based on the large number of paired nucleotides between the ligated primer and the insert. The block on fwd2 can then be removed.

The fwd2 primer may be designed to have relatively low affinity for its target sequence, such that it has a melting temperature of less than 60° C. In this way, a "hot start" extension reaction (starting at a temperature of 60° C. or greater than) would mean that the fwd2 primer would dissociate from the insert before producing a nucleic acid strand. In contrast, the ligated fwd1-fwd2 deblocked primer would remain bound at higher temperature and mediate, using a polymerase with 5'-3' exonuclease activity, (1) producing a nucleic acid strand using the ligated first and second extension primers; and (2) removing all or part of A14'.

Using this method, enriching a target sequence from a sequencing library is performed with both fwd1 and fwd2. Thus, this method has greater specificity for selectively amplifying fragments of interest that comprise a target sequence that binds fwd1 and a target sequence that binds fwd2.

Example 4. Enriching a Target Sequence from a Sequencing Library Using Hairpin Adaptors and Linked Extension Primers In another example, shown in FIG. 4, two primers 90, 92 are linked via a linker 94 that, in an embodiment, is not complementary to the targeted insert sequence, to form a linked extension primer structure 96. The primers 90, 92, illustrated as fwd1 and fwd2 in FIG. 4, are complementary to two different noncontiguous regions of the targeted insert sequence. The melting temperature of the linked extension primer structure is governed by the melting temperature when hybridized to the complementary sequences to the fwd1' and fwd2' primers as shown in FIG. 4 because the linker is not hybridized and, therefore, does not significantly contribute to the melting temperature.

Annealing and extension can occur at a melting temperature greater than the melting temperature of the fwd1 or the fwd2 extension primer alone. The melting temperature is sufficiently high such that, when only one of the fwd1 or fwd2 primers has a complementary sequence, the linked extension primer structure cannot bind. If both primers can bind to the targeted insert sequence, the linked extension primer structure can remain bound for extension. Thus, the higher specificity requirement of two separate sequences being present is realized. The bound linked extension primer structure can be used in an extension reaction using a polymerase with exonuclease activity as generally discussed herein to remove the double-stranded portion of the hairpin adaptor to reveal or unlock the 5' A14 sequence as shown.

The linker may be a universal sequence linking the two different primers. To generate a reaction mixture for a plurality of different targeted insert sequences, each different set of first and second primers can be specific to each respective target sequence of interest. Accordingly, each different target sequence can have a specific first primer and a specific second extension primer. However, the linking sequence for all of the sets may be the same sequence used to link each first primer with its corresponding second primer. This arrangement permits the relatively less expensive custom manufacture of shorter specific sequences that are linked by a common linker sequence. The linker can be designed such that the linker binds to no targeted insert sequences.

Example 5. Enriching a Target Sequence from a Sequencing Library Using Ligated Double-Stranded Adaptors While certain embodiments discussed herein relate to hairpin adaptors, other embodiments may be implemented with extension-mediated double-stranded adaptor ligation, as illustrated in FIG. 5. FIG. 5 shows a comparison between library fragments 12 with inserts 14, whereby some fragments 12 have a targeted insert sequence 14*a* and other fragments 12 do not have a targeted insert sequence 14*b*.

The fragments 12 have end adaptors 100. Each end adaptor includes a first strand 101 and a second strand 102. Portions of the first strand 101 and the second strand 102 are complementary to form a double-stranded region 103. Another portion of the second strand 102 includes a single-stranded 3' terminal region 104 that extends away from a 3' terminus of the double-stranded region 103. The adaptors 100 in the illustrated example of FIG. 5 do not include hairpins.

Denaturation of the fragments to form separated strands permits binding of target-specific extension primers 110 that specifically hybridize to strands 112*a* containing targeted inserts 14*a*. Other strands 112*b*, with inserts 14*b* that do not include target sequences, do not bind to the primers 110 under the reaction conditions. In an embodiment, the method may be used in conjunction with a plurality of target-specific extension primers 110 having different sequences for respective different target sequences.

Extension of a complementary strand from the primer 110 generates a duplex of the complementary strand and the strand 112*a* having a double-stranded end 120 that is not present on the other strands 112*b* with non-target inserts 14*b*. The double-stranded end 120 can be extended to add an A-overhang to be subsequently ligated to a double-stranded adaptor 124. The ligation at the 5' end of the strand 112*a* adaptorizes the 5' end, which can then be amplified to yield full length products 130 with different end adaptors as provided herein that contain the targeted insert 14*a*. For example, each strand of the full length product can have a first amplification primer sequence at a 5' end and a second amplification primer sequence at a 3' end. Amplification may be using indexed primers as discussed herein. While the illustrated example shows A-overhang ligation, the double-stranded end 120 can also be a blunt double-stranded nontemplated ligation to a blunt double-stranded adaptor.

In the illustrated method, the strands 112*b* with non-target inserts 14*b* are not amplified. There is no binding event for the primer 110 and, therefore, no extension to create a double-stranded end. Accordingly, only a single primer 36 of a primer set can bind the non-target strands 112*b*, and there is no amplification of the non-target strands.

Example 6. Library Amplification Results Using Hairpin Adapters and Control Adaptors An experiment was designed to test the effect of PCR amplification of a ligated hairpin adaptor using primers that bind within the hairpin region vs primers that bind within forked regions (positive control). A model 80mer oligonucleotide double-stranded DNA template was synthesized to include 3' single A-overhangs with phosphorylated 5' ends. This model template served as a simple model for a double-stranded DNA sample insert. To this template, two different adaptor types were ligated using Illumina LIG2 reagent at 30° C. for 10 minutes. Control duplex oligo was at 1 uM and adaptors were at 9 uM. Firstly, a control adaptor type was used (see FIG. 7 control adaptor) that contained duplex ME regions, an internal sequence CPH4' and B15' on one fork, and A14 on the other. The other adaptor type contained the same ME duplex regions, the same top strand as the control adaptor, but the bottom strand of the fork contained an additional inner sequence (CPH3) and a hairpin of A14. Adaptors were denatured at 95° C. before being snap cooled on ice to form stocks at 50 uM in Tris-Hcl pH 8, 10 mM NaCl. Note that the hairpin sequence between A14 and A14' was 5 bases in length. Each adaptor was added to separate ligation reactions to create ligated duplexes with either the control adaptor at each end of the duplex, or the hairpin adaptor. PCR amplification of was carried out using either the inner primers (CPH4-ME and A14-i5-P5 for the control forked adaptor, and CPH4-ME and CPH3-ME for the hairpin adaptor) or outer primers (A14-i5-P5 and B15-i7-P7 for both adaptors). The ligated template was diluted 7.5× and mixed with PCR reagent in Illumina PCR mix (EPM). Amplification was carried out using an initial 3 minute denaturation at 95° C. followed by 8 cycles of 95° C. for 20 s, 60 C for 15 s, with a temperature gradient for the extension temp (72° C.-60° C.). The was followed by a final extension of 72° C. for 5 m and then taken to 4° C. Amplification products were quantified using an Agilent D1000 HS Tapestation.

Figure 6:
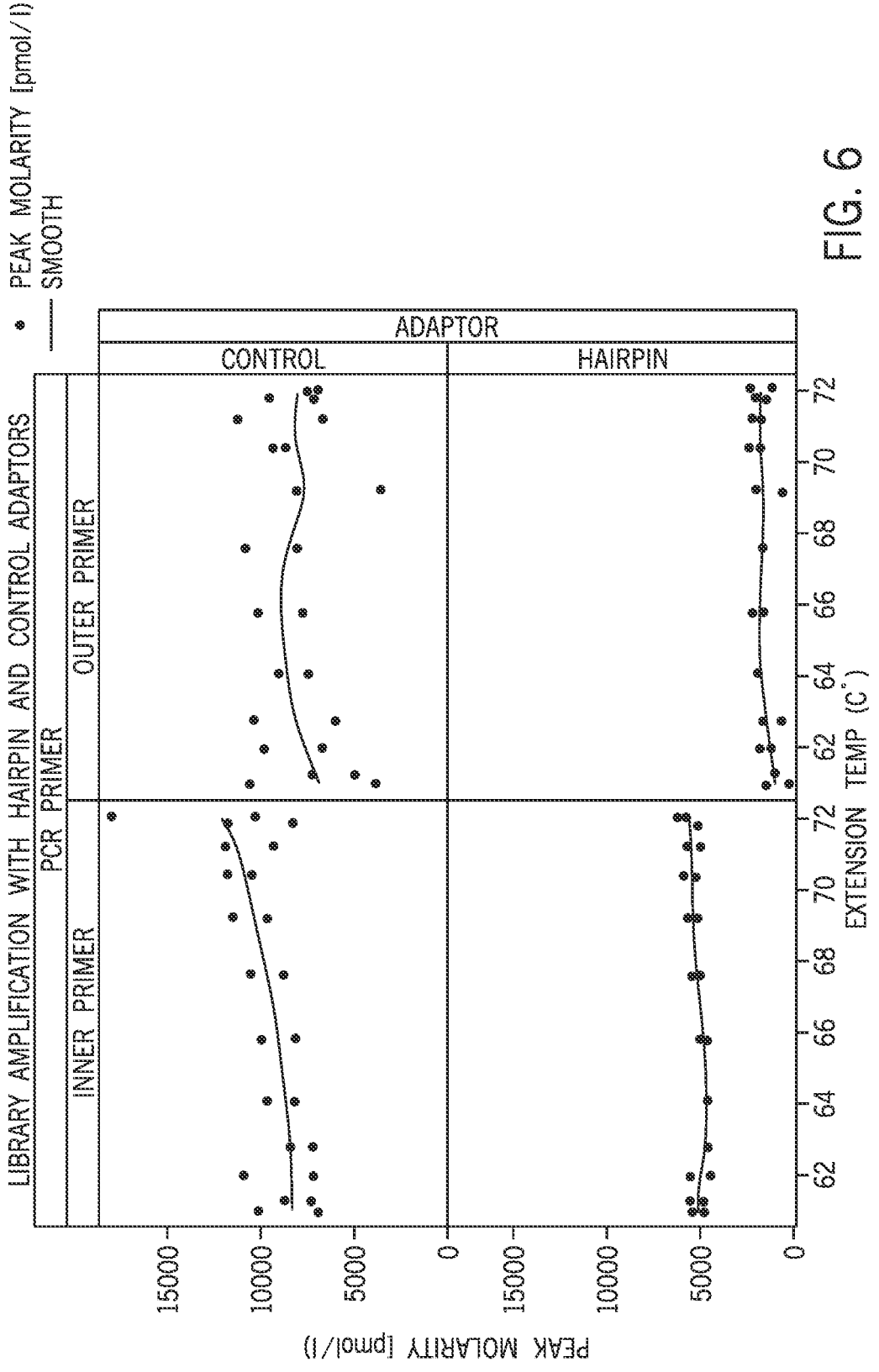
FIG. 6 shows library amplification results using hairpin and control adaptors.
Figure 7:
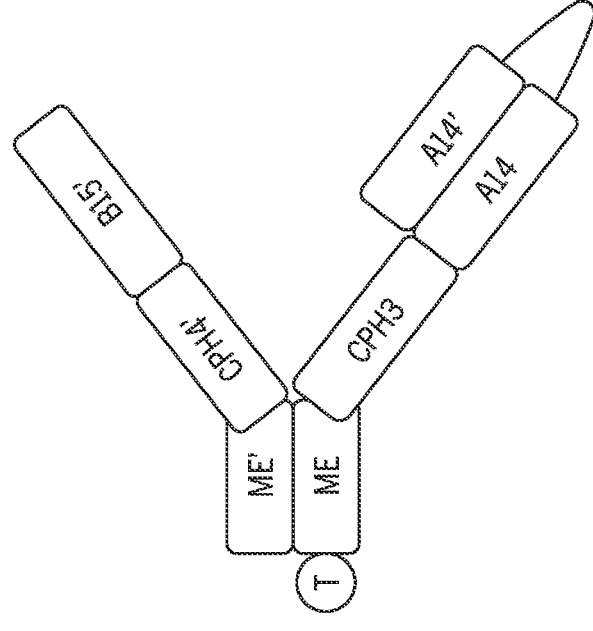
FIG. 7 shows the hairpin and control adaptors used in the library amplification of FIG. 6.
Figure 7:
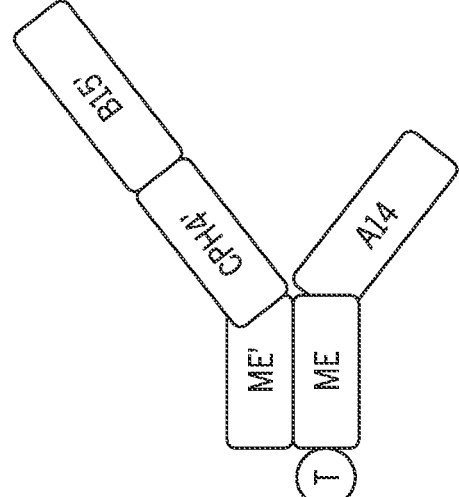

FIG. 6 shows four panels of extension temperature vs. peak molarity, and FIG. 7 shows the control and hairpin adaptor structures used to generate the results in FIG. 6. Little effect is seen from the extension temperature gradient, but the lowest yielding amplification products are clearly seen with the hairpin adaptors when amplified with the outer primers (lower right panel). Control inner primers for the hairpin adaptors clearly show that product can be amplified from the ligated adaptor template with the inner primers, confirming hairpin adaptor ligation. For non-hairpin adaptor libraries, similar yields are observed when PCR is used from inner and outer primer pairs. These data suggest hairpin adaptor sequences inhibit PCR amplification when primer pairs are used that are contained in the hairpin (A14 in this case). In other words, the locked configuration of the hairpin prevents amplification.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. An adaptor for use in preparing a nucleic acid sequencing library comprising:
   a. a first strand having a 5' end and a 3' end; and
   b. a second strand having a 5' end and a 3' end;
   wherein a portion of the 3' end of the first strand and a portion of the 5' end of the second strand are complementary and form a first double-stranded region,
   wherein a portion of the 5' end of the first strand and a portion of the 3' end of the second strand are non-complementary; and
   wherein the portion of the 5' end of the first strand comprises a second double-stranded region and a linker portion, wherein the second double-stranded region comprises an amplification primer sequence hybridized to a sequence complementary to the amplification primer sequence, wherein the linker portion is between the amplification primer sequence and the sequence complementary to the amplification primer sequence and wherein the linker portion is not degradable by an exonuclease.

2. The adaptor of claim 1, wherein the second double-stranded region and the linker portion comprise a hairpin structure.

3. The adaptor of claim 1, wherein the linker portion comprises a non-nucleic acid portion.

4. The adaptor of claim 1, wherein the first double-stranded region is at least 5 consecutive nucleotides.

5. The adaptor of claim 1, wherein the second double-stranded region is at least 5 consecutive nucleotides.

6. The adaptor of claim 1, wherein the 5' end of the second strand is phosphorylated.

7. The adaptor of claim 1, wherein all cytosine bases in the first strand and in the second strand are methylated.

8. The adaptor of claim 1, wherein the adaptor further comprises a capture moiety.

9. A method of preparing a nucleic acid sequencing library comprising:
   a. producing a plurality of double-stranded nucleic acid fragments; and
   b. attaching the adaptor of any one of claim 1-3 or 4-8 to at least one end of the plurality of double-stranded nucleic acid fragments.

10. The method of claim 9, wherein the adaptor is attached via tagmentation.

11. The method of claim 9, wherein the adaptor is attached via ligation.

12. A kit for preparing a nucleic acid sequencing library comprising:
   a. the adaptor of any one of claim 1-3 or 4-8;
   b. at least one primer capable of hybridizing to a portion of the adaptor;
   c. at least one enzyme; and
   d. dNTPs.

13. The kit of claim 12, wherein the at least one enzyme has exonuclease activity.

14. The kit of claim 12, wherein the at least one enzyme is a polymerase.

15. The kit of claim 12, wherein at least one component is in a lyophilized or dried form.

* * * * *